United States Patent
Olivero

(10) Patent No.: US 11,071,717 B2
(45) Date of Patent: Jul. 27, 2021

(54) ANESTHETIC BANDAGE

(71) Applicant: Ana R. Olivero, New Rochelle, NY (US)

(72) Inventor: Ana R. Olivero, New Rochelle, NY (US)

( * ) Notice: Subject to any disclaimer, the term of this patent is extended or adjusted under 35 U.S.C. 154(b) by 0 days.

(21) Appl. No.: 15/652,919

(22) Filed: Jul. 18, 2017

(65) Prior Publication Data

US 2018/0015050 A1    Jan. 18, 2018

Related U.S. Application Data

(60) Provisional application No. 62/363,471, filed on Jul. 18, 2016.

(51) Int. Cl.
*A61K 9/70* (2006.01)
*A61K 9/00* (2006.01)
*A61K 31/167* (2006.01)

(52) U.S. Cl.
CPC .......... *A61K 9/7084* (2013.01); *A61K 9/0014* (2013.01); *A61K 31/167* (2013.01)

(58) Field of Classification Search
None
See application file for complete search history.

(56) References Cited

U.S. PATENT DOCUMENTS 4,460,368 A    7/1984  Allison et al.
5,415,866 A    5/1995  Zook
(Continued)

FOREIGN PATENT DOCUMENTS

JP    1272521 A       10/1989
JP    2003277256 A    10/2003
(Continued)

OTHER PUBLICATIONS

Taghizadeh et al. "A New Liposomal-Drug-in-Adhesive Patch for Transdermal Delivery of Sodium Diclofenac" 2011.*
(Continued)

*Primary Examiner* — Danah Al-Awadi
(74) *Attorney, Agent, or Firm* — Ostrolenk Faber LLP

(57) ABSTRACT

A bandage for delivering an anesthetic through a patient's skin at the site of a hypodermic injection prior to the administration of the hypodermic injection to alleviate pain due to the injection. The bandage has a first layer having a perimeter area adhesive, an anesthetic delivery layer disposed on the first layer inside the perimeter area and containing an anesthetic for delivery into the patient's skin, a first peel-off layer covering the anesthetic delivery layer for keeping the anesthetic delivery layer sterile until the peel-off layer is removed, the first layer being placed on the skin of the patient at the future site of the injection with the anesthetic delivery layer and adhesive being in contact with the skin of the patient thereby to adhere the bandage to the site and allow the anesthetic delivery layer to deliver the anesthetic into the skin, wherein the anesthetic delivery layer comprises a material for accelerating the delivery of the anesthetic into the patient's skin, the anesthetic delivery layer adapted to receive the injection therethrough after the skin has undergone numbing by the anesthetic.

12 Claims, 4 Drawing Sheets

(56) References Cited

U.S. PATENT DOCUMENTS

| | | | |
|---|---|---|---|
| 6,124,522 A * | 9/2000 | Schroeder | A61F 15/001 602/57 |
| 6,274,167 B1 | 8/2001 | Margiotta | |
| 6,461,644 B1 | 10/2002 | Jackson et al. | |
| 7,764,993 B2 | 7/2010 | Kumar et al. | |
| 8,206,336 B2 | 6/2012 | Shantha | |
| 8,282,607 B2 | 10/2012 | Smith et al. | |
| 2004/0191301 A1 * | 9/2004 | Van Duren | A61K 9/7084 424/449 |
| 2005/0080368 A1 * | 4/2005 | Hurwitz | A61F 13/0203 602/2 |
| 2006/0067993 A1 | 3/2006 | Margiotta | |
| 2010/0190004 A1 * | 7/2010 | Gibbins | A61L 15/46 428/346 |
| 2014/0288481 A1 | 9/2014 | Morgan | |
| 2014/0296826 A1 * | 10/2014 | Finke | A61L 15/60 604/506 |

FOREIGN PATENT DOCUMENTS

| | | | |
|---|---|---|---|
| JP | 2007044258 A | | 2/2007 |
| KR | 2004084783 A | | 10/2004 |
| KR | 591765 B1 | | 6/2006 |
| WO | WO-2004/032907 | | 4/2004 |
| WO | WO 2007/048171 | * | 5/2007 |
| WO | WO 2007048171 | * | 5/2007 |
| WO | WO 2013188884 | * | 12/2013 |

OTHER PUBLICATIONS

Definition of Liposome English Oxford Dictionaries.*
Transdermal Patches: A Recent Approach to New Drug Delivery System; Academic Scienses, International Journal of Pharmacy and Pharmaceutical Sciences; ISSN-0975-1491, vol. 3, Suppl 5, 2011; Sonia Dhiman et al.

* cited by examiner

ANESTHETIC BANDAGE

CROSS REFERENCE TO RELATED APPLICATIONS

This application claims the benefit and priority of U.S. Provisional Patent Application No. 62/363,471, filed Jul. 18, 2016, entitled ANESTHETIC BANDAGE, the entire disclosure of which is incorporated by reference herein.

BACKGROUND OF THE INVENTION

The invention relates to a bandage, and in particular to a product to alleviate pain associated with hypodermic injections. The invention provides a way to alleviate the pain associated with many routine vaccines and injections. These treatments are important for a patient's health care, and in particular to children, but often cause patients, and in particular children, and by extension, their parents, discomfort. The invention also helps to prevent the development of negative attitudes during doctor's visits and encourages parents to bring children back for required doctor's visits, thus providing for better medical care for patients. The invention is a new product to be used when administering injections and vaccinations, which will diminish the pain and fear associated with these procedures. Doctor's visits will be far more pleasant for the patients, especially children and their parents, as well as the doctors providing the care.

SUMMARY OF THE INVENTION

The invention is an adhesive bandage having a topical anesthetic with a delivery system on a sterile pad for delivering the anesthetic painlessly through the skin. The bandage can be applied to the skin before a hypodermic injection or vaccine is administered, and the pain normally associated with such injections will be eliminated or reduced by the anesthetic. The injection is delivered through the sterile pad. Preferably, the bandage is multi-layer, having a peel-off layer for maintaining sterility and protecting the anesthetic bandage until use. An adhesive layer is disposed on the perimeter of the layer containing the sterile anesthetic containing pad. A peel-off layer is provided to protect the adhesive. The peel-off layer that protects the adhesive can be the same peel-off layer that maintains sterility of the anesthetic containing pad that is peeled off before affixation to the skin of the patient.

According to one aspect, the invention comprises a bandage for delivering an anesthetic through a patient's skin at the site of a hypodermic injection prior to the administration of the hypodermic injection to alleviate pain due to the injection, comprising a first layer having a perimeter area adhesive; an anesthetic delivery layer disposed on the first layer inside the perimeter area and containing an anesthetic for delivery into the patient's skin; a first peel-off layer covering the anesthetic delivery layer for keeping the anesthetic delivery layer sterile until the peel-off layer is removed; the first layer being placed on the skin of the patient at the future site of the injection with the anesthetic delivery layer and adhesive being in contact with the skin of the patient thereby to adhere the bandage to the site and allow the anesthetic delivery layer to deliver the anesthetic into the skin; wherein the anesthetic delivery layer comprises a material for accelerating the delivery of the anesthetic into the patient's skin; the anesthetic delivery layer adapted to receive the injection therethrough after the skin has undergone numbing by the anesthetic.

According to another aspect, the invention comprises a method for delivering an anesthetic through a patient's skin at the site of a hypodermic injection prior to the administration of the hypodermic injection to alleviate pain due to the injection, the method comprising providing a bandage having a first layer having a perimeter area adhesive, an anesthetic delivery layer disposed on the first layer inside the perimeter area and containing an anesthetic for delivery into the patient's skin, and a first peel-off layer covering the anesthetic delivery layer for keeping the anesthetic delivery layer sterile until the peel-off layer is removed; peeling off the peel-off layer, placing the first layer on the skin of the patient at the future site of the injection with the anesthetic delivery layer and adhesive being in contact with the skin of the patient thereby to adhere the bandage to the site and allow the anesthetic delivery layer to deliver the anesthetic into the skin, the anesthetic delivery layer accelerating the delivery of the anesthetic into the skin; and after a suitable delay to numb the site, administering the injection through the anesthetic delivery layer into the skin.

A further, more detailed explanation of the functionality of the invention will be elaborated upon in the following.

BRIEF DESCRIPTION OF THE DRAWINGS

The invention will now be described in greater detail in the following detailed description, with reference to the drawings, in which.

DETAILED DESCRIPTION

The invention has unique features not presently available in the marketplace.

The invention comprises an adhesive bandage having multiple layers, e.g., two or three or more layers, to be applied to the patient's skin at the injection site before the injection is administered as a way to prevent or reduce the pain normally associated with injections. The bandage is applied to the area of skin before the injection is made and the injection is administered through it. In one embodiment, a peel-off layer is provided to expose an adhesive to allow affixation of the bandage to the skin of the patient. In one embodiment, the peel-off layer also exposes a sterile pad having the anesthetic. The bandage is applied to the site where the injection will be made. Once the topical anesthetic has had sufficient time to numb the skin under the bandage, the injection is administered through the exterior facing layer of the bandage and through the anesthetic pad, affixed to the skin by the adhesive. The bandage remains in place, after the injection has been administered, for a period of time, continuing to provide pain relieving anesthesia to the site.

According to the invention, the anesthetic containing pad is designed to accelerate the delivery of the anesthetic into the skin to reduce the waiting time before the injection can be administered.

Examples of the invention are shown in the accompanying drawings.

Figure 1:
FIG. 1 shows, in perspective view, exemplary embodiments of the bandage and packaging for same.
Figure 2:
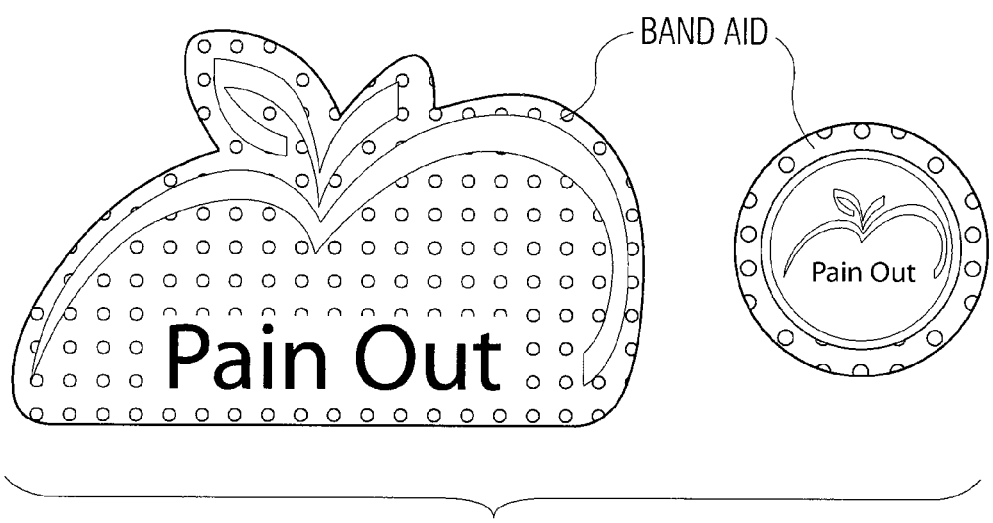
FIG. 2 shows the bandages of FIG. 1 in top plan view.

In particular, FIG. 1 shows an exemplary package for bandages according to the invention and two examples of the bandages. The bandages can take other shapes or forms. FIG. 2 shows the bandages of FIG. 1 in more detail in top plan view, showing examples of the external design. The external shape and design can take other forms. For children, it may be desirable to use pleasing, child-appealing shapes, e.g., cartoon characters, pleasing shapes in the form of toys, fruits, etc. and/or pleasing logos.

Figure 3:
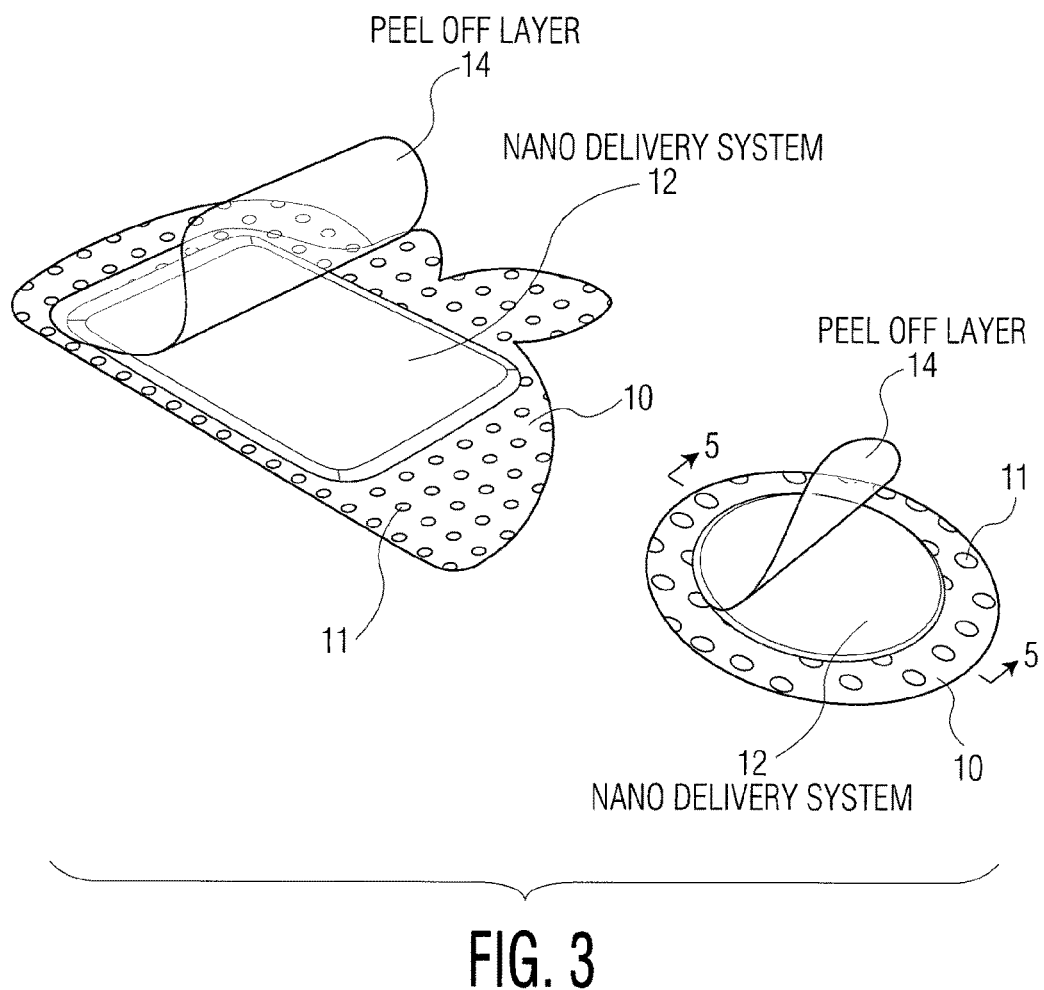
FIG. 3 shows the multi-layer construction of the bandages in perspective view.

FIG. 3 shows two examples of one embodiment of the multi-layer construction including a flexible layer 10 having an adhesive 11 on the perimeter (and preferably protected by a peel-off layer, not shown). The bandage is shown with the skin-facing side up. A sterile anesthetic containing pad 12 is disposed on the layer 10. A peel-off layer 14 protects the sterile pad 12 and maintains sterility until use. The pad 12 contains the anesthetic, which may be any known anesthetic substance desirable for use as a topical anesthetic. The adhesive 1, generally provided as an adhesive layer on the perimeter of the layer 10, can be any suitable medically compatible adhesive used for bandage products. The removable peel-off layer 14 covers the pad 12 to keep it sterile and is peeled-off before the bandage, with the pad 12 facing the skin, is applied to the skin. The injection is made through the layer 10 and pad 12 into the underlying skin or body tissue. The layer 10 may optionally have another peel-off layer to keep the exterior of the layer 10 sterile prior to injection.

According to one embodiment, the sterile anesthetic containing pad may comprise a phase-change material (PCM). Such phase-change materials release or store energy when undergoing a phase change, for example, solid-liquid phase changes, solid-gas phase changes, liquid-gas phase changes, solid-solid phase changes (changes in crystalline structure). Such phase-change materials assist in driving the anesthetic through the patient's skin to accelerate the delivery of the anesthetic.

Typically, PCMs are substances with a high heat of fusion, which, upon melting (solid to liquid) or solidifying (liquid to solid) or undergoing a crystalline structure change (solid-solid) at a certain temperature (e.g. the patient's body temperature), are capable of storing or releasing substantial amounts of energy. The use of a PCM in the invention causes the stored/released energy to be used to drive the anesthetic into the patient's skin.

The patient's body temperature can facilitate the phase change of the PCM.

Figure 4:
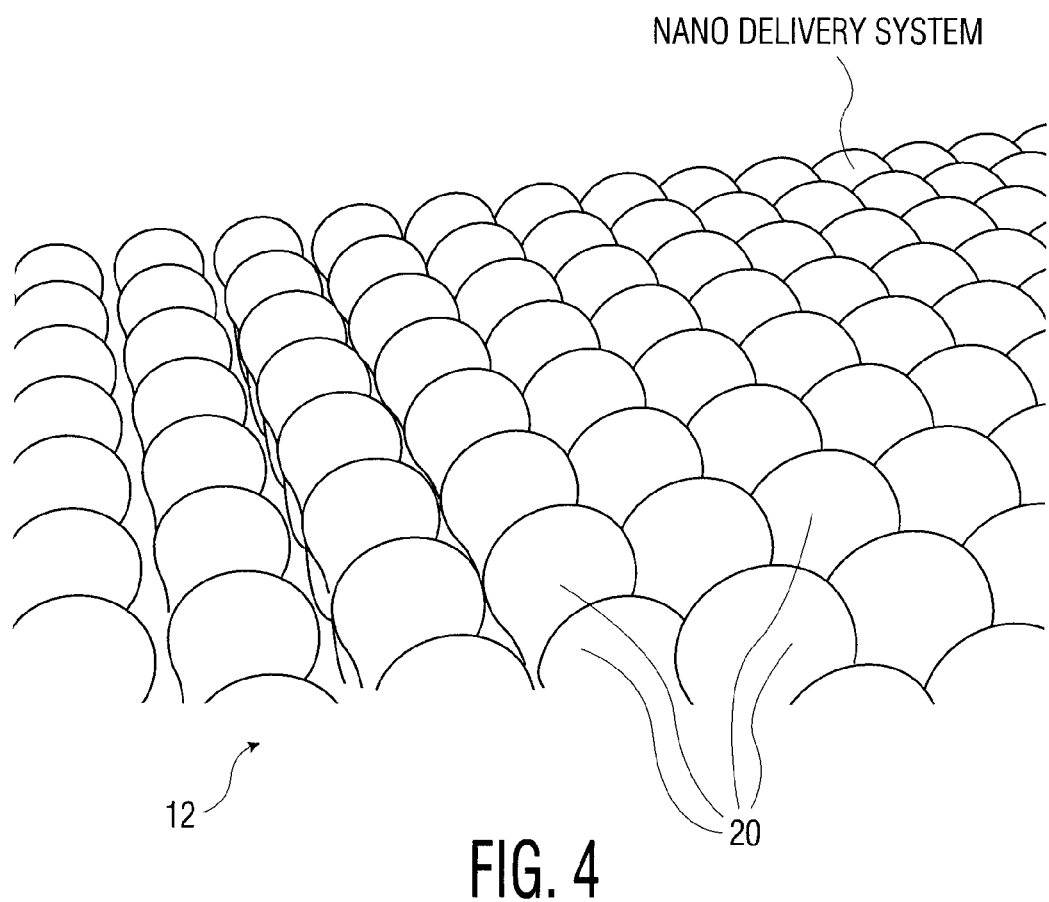
FIG. 4 shows details of one example of an anesthetic delivery system.

According to the invention, the sterile pad 12 may include a nano delivery system for delivering the anesthetic into the body tissue as shown in FIG. 4 in a greatly enlarged view. The nano-size projecting features 20 (on the order of a few nanometers or less) help to provide a faster, more efficient delivery of the anesthetic into the body tissue. It is also possible to use micron-scale features.

The nano delivery system can be combined with the phase-change material so that the nano delivery system incorporates a phase-change material to facilitate fast delivery of the anesthetic.

Another example of the anesthetic delivery system comprises the use of liposomes, minute spherical sacs of phospholipid molecules enclosing a water droplet, especially as formed artificially to carry drugs (e.g. anesthetic) or other substances into the tissues.

Examples of anesthetics that can be used in the invention include topical anesthetics such as Lidocaine and/or Prilocaine. Other anesthetics can be employed.

Logos or other pleasing designs may be provided on the perimeter regions of layer 10 and/or on removable peel off layer 14, as well as on the (viewable when installed) exterior of layer 10 and on any other peel-off layer, e.g. for adhesive 11. The layer 10 can take pleasing shapes, for example, shapes pleasing to a child.

Figure 5:
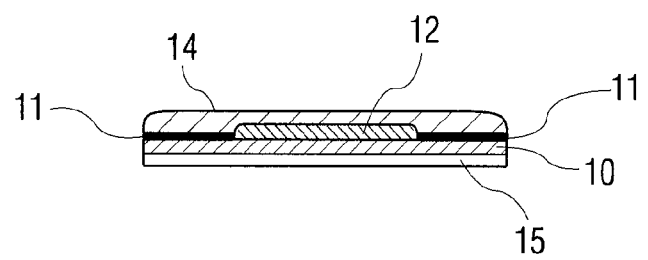
FIG. 5 shows a cross section through the bandage.

FIG. 5 shows the bandage in a cross section, showing the layer 10 with adhesive perimeter layer portions 11. The peel-off layer 14 protects the anesthetic delivery pad 12. In one embodiment, as shown, the peel-off layer 14 protects the adhesive layer 11 as well as the anesthetic pad 12. In another embodiment, two peel-off layers are provided, a first outer peel-off layer covering both the adhesive layer and the anesthetic pad and a second underlying peel-off layer covering only the anesthetic pad. In this second embodiment, the two peel-off layers need to be removed before the bandage is applied to the patient's skin. Also, a further peel-off layer 15 may optionally be provided on the exterior of layer 10 to keep it sterile prior to the injection administered through the layer 10 and anesthetic pad layer 12.

Layers 10 and 14 and any other peel-off layer can be made from suitable flexible medical plastic/cloth materials. The anesthetic pad 12 can be a gauze pad, or another sterile medical tissue covering material that can absorb and deliver the anesthetic. As explained above, pad 12 may include a phase-change material (PCM) and/or have nano-scale or micron-scale features.

The unique features of the invention will provide the following benefits for all babies, children, their parents and their doctors as well as other patients, e.g., adults:

Pain associated with vaccines and injections in patients will be alleviated

Doctor's visits will be far more pleasant for the patients and their parents

Children may not develop fearful and negative opinions about doctor visits

The doctors and medical personnel administering injections will no longer be responsible for causing pain and making their patients cry and the pain associated with injections will be appreciably reduced.

The cost of materials and actual materials used will depend on the quantity manufactured but it is envisioned that known medical adhesives, plastics and peel-off layers may be used in production. As particular models or sizes expand, the invention can be modified or corrected for improvement. Measurements/dimensions may be subject to subsequent changes that may enhance the product.

The invention is believed to appeal to medical care providers who administer vaccinations and injections and, in particular, to babies and children. Today's society is always seeking new ways to make providing health care less traumatic for these patients, and this product addresses this need. Doctors using this product will be eliminating or reducing the pain normally associated with injections, and the patients and their parents will be less fearful and anxious about returning the next time.

It is believed that medical care providers and their patients worldwide will appreciate the benefits of using this product when injections must be administered. This product can be made available through medical suppliers who provide the medications and syringes doctors and technicians use in hospital and clinic settings. The Internet may provide an additional important platform for the advertising and marketing of this product.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A bandage for delivering an anesthetic through a patient's skin at the site of a hypodermic injection prior to the administration of the hypodermic injection to alleviate pain due to the injection, comprising:
   a first layer having a perimeter area adhesive on a first surface thereof, the perimeter area adhesive having edges, the first layer having a sterile second surface opposite the first surface;
   an anesthetic delivery layer disposed on the first surface of the first layer and having edges spaced from and located inside the edges of the perimeter area adhesive, the anesthetic delivery layer comprising a sterile pad that contains an anesthetic for delivery into the patient's skin, the sterile pad being inside of the perimeter area adhesive and having edges spaced from the edges of the perimeter area adhesive;
   a first peel-off layer covering the sterile pad of the anesthetic delivery layer to keep the sterile pad of the anesthetic delivery layer sterile until the first peel-off layer is removed;
   the sterile pad of the anesthetic delivery layer of the first layer being placed on the skin of the patient at the future site of the injection and the perimeter area adhesive being in contact with the skin of the patient, wherein the perimeter area adhesive adheres the bandage to the site and allows the anesthetic delivery layer to deliver the anesthetic into the skin; and
   a second peel-off layer on the second surface of the first layer that, until the second peel-off layer is removed from the second surface of the first layer, keeps at least a portion of the second surface of the first layer sterile at least long enough to permit the site of the hypodermic injection to become numb by contact with the sterile pad that contains the anesthetic,
   wherein the portion of the second surface of the first layer that is kept sterile after the first peel-off layer is removed and the sterile pad is placed in contact with the site of the hypodermic injection is located over the sterile pad,
   wherein the second peel-off layer extends at least over the entirety of the anesthetic delivery layer;
   wherein the anesthetic delivery layer comprises a material for accelerating the delivery of the anesthetic into the patient's skin;
   wherein the sterile pad of the anesthetic delivery layer and the first layer permit the administration of the hypodermic injection therethrough after the skin has undergone numbing by the anesthetic.

2. The bandage of claim 1, wherein the first peel-off layer protects both the perimeter area adhesive and the anesthetic delivery layer.

3. The bandage of claim 1, further comprising a second peel-off layer covering both the first peel-off layer and the perimeter area adhesive.

4. The bandage of claim 1, wherein the anesthetic delivery layer comprises a plurality of anesthetic absorbent surfaces for delivering the anesthetic into the patient's skin.

5. The bandage of claim 4, wherein the anesthetic delivery layer comprises a plurality of nano-scale or micron-scale projecting surfaces.

6. The bandage of claim 1, wherein the anesthetic delivery layer comprises a phase-change material that changes phase at the body temperature to store energy to accelerate the delivery of the anesthetic into the patient's skin.

7. The bandage of claim 1, wherein the anesthetic delivery layer comprises a liposome.

8. The bandage of claim 7, wherein the liposome comprises a spherical sac of a phospholipid molecule enclosing a water droplet.

9. The bandage of claim 1, wherein the anesthetic comprises a topical anesthetic.

10. The bandage of claim 1, wherein the second surface of the first layer has decoration visible when the bandage is applied to the skin of the patient.

11. The bandage of claim 1, wherein the perimeter area adhesive has a surface that makes contact with the skin of the patient, and the anesthetic delivery layer has a surface that makes contact with the skin of the patient that is spaced from the surface of the perimeter area adhesive that makes contact with the patient's skin, and
   wherein the sterile pad is a gauze pad.

12. The bandage of claim 1, wherein the anesthetic comprises either Lidocaine or Prilocaine.

* * * * *